(12) United States Patent
Atkinson et al.

(10) Patent No.: US 6,277,839 B1
(45) Date of Patent: Aug. 21, 2001

(54) BIPHENYLENE LACTAMS AS PROSTAGLANDIN RECEPTOR LIGANDS

(75) Inventors: Joseph G. Atkinson, Vancouver; Marc Labelle, St-Lazare; Patrick Lacombe, Montreal; Rejean Ruel, Saint-Lazare, all of (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/410,583

(22) Filed: Oct. 1, 1999

Related U.S. Application Data

(60) Provisional application No. 60/103,371, filed on Oct. 7, 1998.

(51) Int. Cl.[7] ............. C07D 225/08; C07D 409/12; A61K 31/395
(52) U.S. Cl. ............. 514/183; 540/455; 540/461
(58) Field of Search .................. 540/455, 461; 514/183

(56) References Cited

FOREIGN PATENT DOCUMENTS

| 0 480 641 A1 | 4/1992 | (EP) . |
|---|---|---|
| 0 752 421 A1 | 1/1997 | (EP) . |

*Primary Examiner*—Bruck Kifle
(74) *Attorney, Agent, or Firm*—Raynard Yuro; Richard C. Billups; David L. Rose

(57) ABSTRACT

The present invention relates to biphenylene lactams of Formula II which are ligands at the prostaglandin receptors, as well as a method for treating prostaglandin mediated diseases comprising administration to a patient in need of such a treatment of a non-toxic therapeutically effective amount of compound of Formula II, and the like.

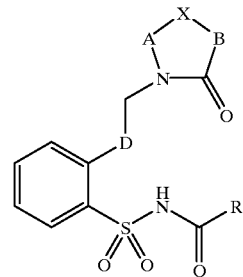

II

7 Claims, No Drawings

BIPHENYLENE LACTAMS AS PROSTAGLANDIN RECEPTOR LIGANDS

CROSS REFERENCE TO RELATED APPLICATIONS

This application is a non-provisional application related to U.S. application Ser. No. 60/103,371, filed on Oct. 7, 1998 priority of which is claimed hereunder.

BACKGROUND OF THE INVENTION

This invention relates to compounds and methods for treating prostaglandin mediated diseases, certain pharmaceutical compositions thereof, and the like. More particularly, the compounds of the invention are structurally different from nonsteroidal anti-inflammatory drugs (NSAIDs) and opiates, and are antagonists of the pain and inflammatory effects of E-type prostaglandins.

Two review articles describe the characterization and therapeutic relevance of the prostanoid receptors as well as the most commonly used selective agonists and antagonists: *Eicosanoids: From Biotechnology to Therapeutic Applications*, Folco, Samuelsson, Maclouf, and Velo eds, Plenum Press, New York, 1996, chap. 14, 137–154 and Journal of Lipid Mediators and Cell Signalling, 1996, 14, 83–87. An article from *The British Journal of Pharmacology* (1994, 112, 735–740) suggests that Prostaglandin $E_2$ ($PGE_2$) exerts allodynia through the $EP_1$ receptor subtype and hyperalgesia through $EP_2$ and $EP_3$ receptors in the mouse spinal cord.

Thus, selective prostaglandin ligands, agonists or antagonists, depending on which prostaglandin E receptor subtype is being considered, will have anti-inflammatory, antipyretic and analgesic properties similar to a conventional non-steroidal anti-inflammatory drug and, in addition, will inhibit hormone-induced uterine contractions and have potential anti-cancer effects, but will have a diminished ability to induce some of the mechanism-based side effects of NSAIDs which are indiscriminate cyclooxygenase inhibitors. In particular, such a compound should have a reduced potential for gastrointestinal toxicity, a reduced potential for renal side effects, a reduced effect on bleeding times and a lessened ability to induce asthma attacks in aspirin-sensitive asthmatic subjects. In *The American Physiological Society* (1994, 267, R289-R-294), studies suggest that $PGE_2$-induced hyperthermia in the rat is mediated predominantly through the $EP_1$ receptor. World patent applications WO 96/06822 (Mar. 7, 1996), WO 96/11902 (Apr. 25, 1996) and EP 752421-A1 (Jan. 8, 1997) disclose compounds represented by Formula I as being useful in the treatment of prostaglandin mediated diseases.

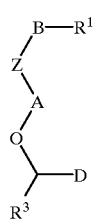

I

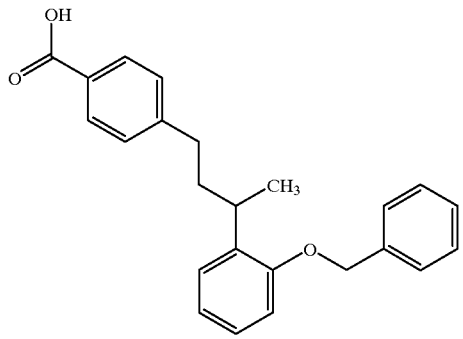

Ia wherein:

A is phenyl, naphthyl, 5- or 6-membered heteroaryl;

B is phenyl, 5- or 6-membered heteroaryl or a keto-dihydro ring;

D is phenyl, 5- or 6-membered heteroaryl;

$R^1$ is COOH, $(CH_2)_n$COOH, tetrazolyl(alkyl);

$R^3$ is H, alkyl;

Z is an alkylene bridge;

Ia is one of the compounds specifically claimed.

SUMMARY OF THE INVENTION

The present invention relates to biphenylene lactams which are ligands at the prostaglandin receptors, as well as a method for treating prostaglandin mediated diseases comprising administration to a patient in need of such a treatment of a non-toxic therapeutically effective amount of compound of Formula II, and the like.

DETAILED DESCRIPTION OF THE INVENTION

An embodiment of the present invention is a compound of structural Formula II:

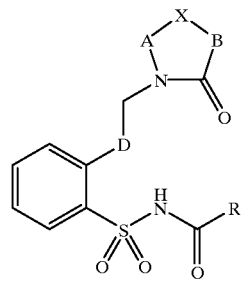

II or a pharmaceutically acceptable salt, crystal form, or hydrate thereof, wherein:

A and B are independently unsubstituted, monosubstituted or disubstituted ortho-benzenediyl or ortho-heteroarylenediyl wherein the substituents are selected from the group consisting of:
a) halogen,
b) $C_{1-5}$ alkyl,
c) $C_{1-5}$ alkoxy,
d) $C_{1-5}$ alkylthio,
e) nitro,
f) CN, g) $C_{1-5}$ fluoroalkyl,
h) $COOR^3$, and
i) $NR^3{}_2$;

X is $CH_2CH_2$, $CH=CH$, $CH_2Y$, $YCH_2$, $CH_2CH_2CH_2$, ortho-benzenediyl or ortho-heteroarylenediyl;

Y is O, S, $CF_2$, or $C=O$;

D is unsubstituted, monosubstituted, or disubstituted benzendiyl wherein the substituents are selected from:
a) halogen,
b) $C_{1-5}$ alkyl,
c) $C_{1-5}$ alkoxy,
d) $C_{1-5}$ alkylthio,
e) nitro,
f) CN,
g) $C_{1-5}$ fluoroalkyl,
h) $COOR^3$, and
i) $NR^3{}_2$;

R is:
a) $C_{1-6}$ alkyl,
b) $(CR^1R^2)_n O$—Ph,
c) $(CR^1R^2)_n$O-heteroaryl,
d) $O-(CR^1R^2)_n$Ph,
e) $O-(CR^1R^2)_n$heteroaryl,
f) $NR^3-(CR^1R^2)_n$Ph,
g) $NR^3-(CR^1R^2)_n$heteroaryl,
h) $C_{2-6}$ alkenyl-Ph,
i) $C_{2-6}$ alkenyl-heteroaryl,
j) $(CR^1R^2)_n$Ph, or
k) $(CR^1R^2)_n$heteroaryl,
wherein Ph or heteroaryl is unsubstituted, monosubstituted or disubstituted with substituents selected from:
1) halogen,
2) $C_{1-5}$ alkyl,
3) $C_{1-5}$ alkoxy,
4) $C_{1-5}$ alkylthio,
5) nitro,
6) CN,
7) $C_{1-5}$ fluoroalkyl,
8) $COOR^3$, and
9) $NR^3{}_2$;

n=0, 1, 2 or 3;

$R^1$ and $R^2$ are independently hydrogen, $C_{1-3}$ alkyl, benzyl, $C_{1-3}$ fluoroalkyl, $C_{1-3}$ alkoxy, or fluorine;

$R^3$ is H or $C_{1-6}$ alkyl.

A subembodiment of the invention is the compound of structural Formula II as recited above, wherein:

A and B are independently unsubstituted, monosubstituted or disubstituted ortho-benzenediyl wherein the substituents are selected from the group consisting of:
a) halogen,
b) $C_{1-5}$ alkyl,
c) $C_{1-5}$ alkoxy,
d) $C_{1-5}$ alkylthio,
e) nitro,
f) CN,
g) $C_{1-5}$ fluoroalkyl,
h) $COOR^3$, and
i) $NR^3{}_2$;

X is $CH_2CH_2$, $CH=CH$, $CH_2Y$, $YCH_2$, $CHCH_2CH$, ortho-benzenediyl or ortho-heteroarylenediyl;

Y is O or S;

D is unsubstituted or monosubstituted benzendiyl wherein the substituents are selected from:
a) halogen,
b) $C_{1-3}$ alkyl,
c) $C_{1-3}$ alkoxy,
d) $C_{1-3}$ alkylthio,
e) nitro,
f) CN,
g) $C_{1-3}$ fluoroalkyl,
h) $COOR^3$, and
i) $NR^3{}_2$;

R is:
a) $C_{1-6}$ alkyl,
b) $(CR^1R^2)_n O$—Ph,
c) $O-(CR^1R^2)_n$Ph,
d) $NR^3-(CR^1R^2)_n$Ph,
e) $NR^3-(CR^1R^2)_n$heteroaryl,
f) $C_{2-6}$ alkenyl-Ph, or
g) $(CR^1R^2)_n$Ph,
wherein Ph or heteroaryl is unsubstituted, monosubstituted or disubstituted with substituents selected from:
1) halogen,
2) $C_{1-3}$ alkyl,
3) $C_{1-3}$ alkoxy,
4) $C_{1-3}$ alkylthio,
5) nitro,
6) CN,
7) $C_{1-3}$ fluoroalkyl,
8) $COOR^3$, and
9) $NR^3{}_2$;

n=0, 1, 2 or 3;

$R^1$ and $R^2$ are independently hydrogen, $C_{1-3}$ alkyl, $C_{1-3}$ fluoroalkyl, or $C_{1-3}$ alkoxy;

$R^3$ is H or $C_{1-6}$ alkyl.

A most preferred embodiment of the invention is the compound of structural Formula II above, wherein:

A and B are independently unsubstituted, monosubstituted or disubstituted ortho-benzenediyl wherein the substituents are halogen;

X is $CH_2CH_2$, $CH=CH$, or $OCH_2$;

D is benzendiyl;

R is:
a) $C_{1-3}$ alkyl,
b) $(CR^1R^2)_n O$—Ph,
c) $O-(CR^1R^2)_n$Ph,
d) $NR^3-(CR^1R^2)_n$Ph,
e) $NR^3-(CR^1R^2)_n$thienyl,
f) $C_{2-3}$ alkenyl-Ph, or
g) $(CR^1R^2)_n$Ph,
wherein Ph is unsubstituted or monosubstituted with halogen;

n=0,1, 2 or 3;

$R^1$ and $R^2$ are independently hydrogen, $C_{1-3}$ alkyl, $C_{1-3}$ fluoroalkyl, or $C_{1-3}$ alkoxy;

$R^3$ is H or $C_{1-3}$ alkyl.

Another embodiment of the present invention is a method for treating or preventing a prostaglandin mediated condition comprising administration to a mammalian patient in need of such a treatment of a non-toxic therapeutically effective amount of a compound of Formula II above. A preferred prostaglandin mediated condition is inflammation. Yet another embodiment of the invention is a method for treating or preventing a prostaglandin mediated condition in a mammal, comprising the administration of a non-toxic therapeutically effective amount of a compound of Formula II and a nonsteroidal anti-inflammatory drug. Preferred nonsteroidal anti-inflammatory drugs are aspirin, ibuprofen, naproxen, and ketoprofen. Another embodiment of the invention is a method for treating or preventing a prostaglandin mediated condition in a mammal, comprising the administration of a non-toxic therapeutically effective amount of a compound of Formula II as recited in claim 1 and a cyclooxygenase-2 (COX-2) selective inhibitor. Examples of such COX-2 inhibitors are disclosed in U.S. Pat. Nos. 5,474,995; 5,633,272; and 5,466,823; and in WO 96/25405, WO 97/38986, WO 98/03484, WO 97/14691, and WO 95/0051.

Preferred prostaglandin mediated conditions are rheumatic fever, influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), Paget's disease, gout and ankylosing spondylitis, bursitis, burns including radiation and corrosive chemical injuries, sunburns, pain following surgical and dental procedures, immune diseases, autoimmune diseases, diabetic retinopathy, asthma, Alzheimer's disease, eosinophil related disorders, tumor angiogenesis, cytotoxicity due to chemotherapy, glaucoma, and cancer.

Yet another embodiment is a pharmaceutical composition comprising a pharmaceutically acceptable carrier and a compound of Formula II or a pharmaceutically acceptable crystal form or hydrate thereof, with or without a nonsteroidal anti-inflammatory. Preferred nonsteroidal anti-inflammatories are aspirin, ibuprofen, naproxen, and ketoprofen. Another subembodiment of the invention is a pharmaceutical composition comprising a pharmaceutically acceptable carrier, a compound of Formula II, or a pharmaceutically acceptable crystal form or hydrate thereof, and a cyclooxygenase-2 (COX-2) selective inhibitor. Preferred COX-2 inhibitors are those disclosed in U.S. Pat. No. 5,474,995, and celecoxib.

The terms alkyl, alkenyl, and alkynyl mean linear, branched, and cyclic structures and combinations thereof. The term "alkyl" includes "cycloalkyl" and "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

"Lower alkyl" includes "lower cycloalkyl" and means alkyl groups of from 1 to 7 carbon atoms. Examples of lower alkyl groups include methyl, ethyl, propyl, isopropyl, butyl, s- and t-butyl, pentyl, hexyl, heptyl, and the like.

"Cycloalkyl" includes "lower cycloalkyl" and means a hydrocarbon, containing one or more rings of from 3 to 12 carbon atoms, with the hydrocarbon having up to a total of 20 carbon atoms. Examples of cycloalkyl groups are cyclopropyl, cyclopentyl, cyclo-heptyl, aldamantyl, cyclododecylmethyl, 2-ethyl-1-bicyclo[4.4.0]decyl, and the like.

"Lower cycloalkyl" means a hydrocarbon containing one or more rings of from 3 to 7 carbon atoms, with the hydrocarbon having up to a total of 7 carbon atoms. Examples of lower cycloalkyl groups are cyclopropyl, cyclopropylmethyl, cyclobutyl, 2-cyclopentylethyl, cycloheptyl, bicyclo[2.2.1]hept-2-yl, and the like.

The term "alkenyl" includes "cycloalkenyl" and "lower alkenyr" and means alkenyl groups of 2 to 20 carbon atoms. Examples of alkenyl groups include allyl, 5-decen-1-yl, 2-dodecen-1-yl, and the like.

"Lower alkenyl" includes "lower cycloalkenyl" and means alkenyl groups of 2 to 7 carbon atoms. Examples of lower alkenyl groups include vinyl, allyl, isopropenyl, pentenyl, hexenyl, heptenyl, 1-propenyl, 2-butenyl, 2-methyl-2-butenyl, and the like.

"Cycloalkenyl" includes "lower cycloalkenyl" and means alkenyl groups of 3 to 20 carbon atoms, which include a ring of 3 to 12 carbon atoms, and in which the alkenyl double bond may be located anywhere in the structure. Examples of cycloalkenyl groups are cyclopropen-1-yl, cyclohexen-3-yl, 2-vinyladamant-1-yl, 5-methylene-dodec-1-yl, and the like.

"Lower cycloalkenyl" means alkenyl groups of 3 to 7 carbon atoms, which include a ring of 3 to 7 carbon atoms and in which the double bond may be located anywhere in the structure. Examples of lower cycloalkenyl groups are cyclopropen-1-yl, cyclohexen-3-yl, 2-cyclopentylethen-1-yl, and the like.

The term "heteroaryl" as utilized herein, unless specifically defined otherwise, is intended to include the following: a 5 or 6-membered ring substituted with one, two or three heteroatoms selected from O, S, N, and is unsubstituted or substituted with one or two substituents selected from the group consisting of: halogen, $C_{1-3}$ alkyl, $C_{1-3}$ alkoxy, $C_{1-3}$ alkylthio, nitro, CN, $C_{1-3}$ fluoroalkyl, $COOR^3$, and $NR^3{}_2$; any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, pyrazinyl, pyridazinyl, pyridinyl, pyrimidinyl, and pyrrolyl which are substituted or unsubstituted as defined above.

The term "Ph" as used herein is intended to mean a phenyl substituent that is unsubstituted or substituted with one or two substituents selected from the group consisting of: halogen, $C_{1-3}$ alkyl, $C_{1-3}$ alkoxy, $C_{1-3}$ alkylthio, nitro, CN, $C_{1-3}$ fluoroalkyl, $COOR^3$, and $NR^3{}_2$; any two adjacent substituents can be joined to form to form a benzo-fused ring. Examples of Ph substituents include but are not limited to phenyl and naphthyl.

The heteroaryl group may be optionally substituted with the substituents listed above at any available carbon atom or nitrogen atom (if present), but compounds bearing certain substitutents, directly substituted to a nitrogen may be relatively unstable and are not preferred. The heteroaryl may also be fused to a second 5-, 6-, or 7-membered ring containing one or two oxygens such as: dioxolanyl, dihydrofuranyl, dihydropyranyl, and dioxanyl.

As used herein, the terms "benzenediyl" and "heteroarylenediyl" are intended to mean disubstituted heteroaryl and Ph as defined above. Unless specifically mentioned otherwise, the substitution may be para, meta, or ortho.

It is intended that the definition of any substituent (e.g., $R^6$, $R^{10}$, etc.) in a particular molecule be independent of its definition elsewhere in the molecule. Thus, —N(R³)₂ represents —NHH, —NHCH₃, —NHC₆H₅, etc.

As used herein, the term "composition" is intended to encompass a product comprising the specified ingredients in the specified amounts, as well as any product which results, directly or indirectly, from combination of the specified ingredients in the specified amounts.

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The pharmaceutical compositions of the present invention comprise a compound of Formula II as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula II are meant to also include the pharmaceutically acceptable salts.

Dose Ranges

The magnitude of prophylactic or therapeutic dose of a compound of Formula II will, of course, vary with the nature and the severity of the condition to be treated and with the particular compound of Formula II and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 2 g of an active ingredient, typically 25 mg, 50 mg, 100 mg, 200 mg, 300 mg, 400 mg, 500 mg, 600 mg, 800 mg, or 1000 mg.

Pharmaceutical Compositions

For the treatment of any of the prostanoid mediated diseases compound II may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. No. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound II may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols. For topical use, creams, ointments, gels, solutions or suspensions, etc., containing the compound of Formula II are employed. (For purposes of this application, topical application shall include mouth washes and gargles.) Topical formulations may generally be comprised of a pharmaceutical carrier, cosolvent, emulsifier, penetration enhancer, preservative system, and emollient.

Utilities

The ability of the compounds of Formula II (i.e., Compound II) to interact with prostaglandin receptors makes them useful for preventing or reversing undesirable symptoms caused by prostaglandins in a mammalian, especially human subject. This mimicking or antagonism of the actions of prostaglandins indicates that the compounds and pharmaceutical compositions thereof are useful to treat, prevent, or ameliorate in mammals and especially in humans: Pain, fever and inflammation of a variety of conditions including rheumatic fever, symptoms associated with influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures as well as immune and autoimmune diseases. In addition, such a compound may inhibit cellular neoplastic transformations and metastic tumor growth and hence can be used in the treatment of cancer. Compound II may also be of use in the treatment and/or prevention prostaglandin-mediated proliferation disorders such as may occur in diabetic retinopathy and tumor angiogenesis. Compound II will also inhibit prostanoid-induced smooth muscle contraction by antagonizing contractile prostanoids or mimicking relaxing prostanoids and hence may be use in the treatment of dysmenorrhea, premature labor, asthma and eosinophil related disorders. It will also be of use in the treatment of Alzheimer's disease, the treatment of glaucoma, for the prevention of bone loss (treatment of osteoporosis) and for the promotion of bone formation (treatment of fractures) and other bone diseases such as Paget's disease.

By virtue of its prostanoid or prostanoid antagonist activity, Compound II will prove useful as an alternative to conventional non-steroidal anti-inflammatory drugs (NSAID'S) particularly where such non-steroidal anti-inflammatory drugs may be contraindicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; thrombosis, occlusive vascular diseases; those prior to surgery or taking anti-coagulants. Compound II will also be useful as a cytoprotective agent for patients under chemotherapy. In addition, compounds of Formula II may be combined with conventional nonsteroidal anti-inflammatory drugs (NSAIDs), such as aspirin, ibuprofen, ketoprofen, and naproxen.

Similarly, compounds of Formula II, will be useful as a partial or complete substitute for conventional NSAIDs in preparations wherein they are presently co-administered with other agents or ingredients. Thus in further aspects, the invention encompasses pharmaceutical compositions for treating prostaglandin mediated diseases as defined above comprising the compound of Formula II as defined above and one or more ingredients such as another pain reliever including acetominophen or phenacetin; a potentiator including caffeine; an H2-antagonist; aluminum or magnesium hydroxide; simethicone; a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a diuretic; a sedating or non-sedating antihistamine; a cyclooxygenase-2 (COX-2) inhibitor. Examples of such COX-2 inhibitors are disclosed in U.S. Pat. Nos. 5,474,995; 5,633,272; and 5,466,823; and in WO 96/25405, WO 97/38986, WO 98/03484, WO 97/14691, and WO 95/0051. In addition the invention encompasses a method of treating prostaglandin mediated diseases, comprising: administration to a patient in need of such treatment a non-toxic therapeutically effect amount of the compound of Formula II, optionally co-administered with one or more of such ingredients as listed immediately above.

METHODS OF SYNTHESIS

Compounds of the present invention can be prepared according to the following methods. Other synthetic routes will be immediately apparent to those skilled in the art.

Preparation of Intermediates

Biphenyl Sulfonamides:

As shown in Scheme I, 2-bromobenzenesulfonyl chloride III (purchased from Lancaster) is reacted with tert-butylamine. The resulting sulfonamide IV is converted, via a palladium-catalyzed coupling with boronic acid V (purchased from Omega Chemical Company Inc.) to biphenyl derivative VI. When treated with HBr in acetic acid, activation of the hydroxyl group and deprotection occur in the same procedure to afford sulfonamide VII. This sulfonamide is a common intermediate used in alkylation reactions with azocinones (dibenzolactams).

SCHEME 1

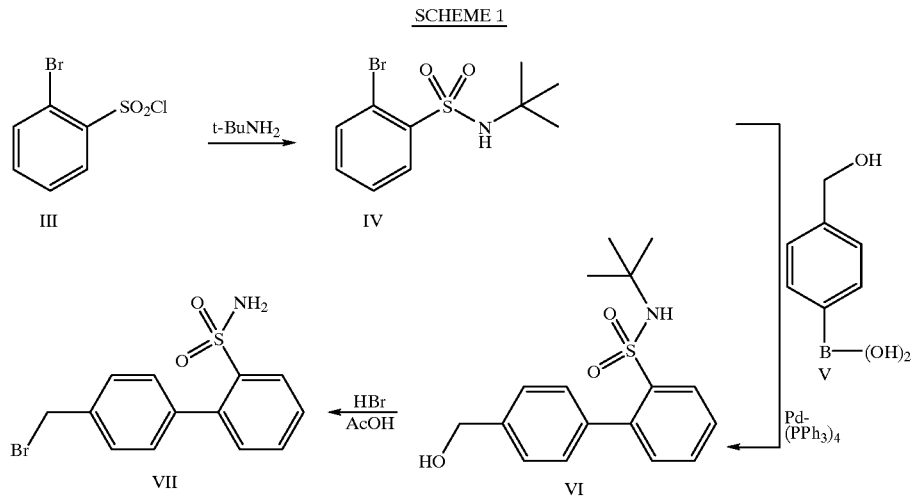

Substituted boronic acids can also be prepared according to the following scheme:

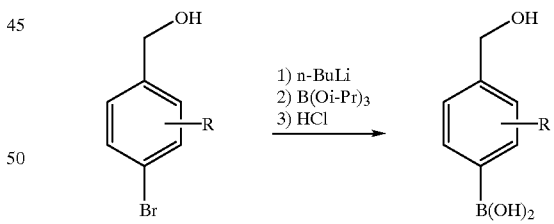

Synthesis of Compounds

Azocinones (dibenzolactams):

Tetrahydrodibenz[b,f]azocin-6-one (VIII), shown in Scheme 2, is commercially available from Aldrich Chemical Co., Inc., in Milwaukee, Wis. The corresponding unsaturated compound IX can be prepared (VIII can also be prepared in the same manner from dibenzosuberone) from commercially available dibenzosuberenone (X) via a two-step sequence (i-oxime formation using hydroxylamine and ii-Beckmann rearrangement on the corresponding tosylate) as shown in Scheme 2.

SCHEME 2

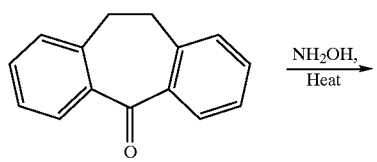

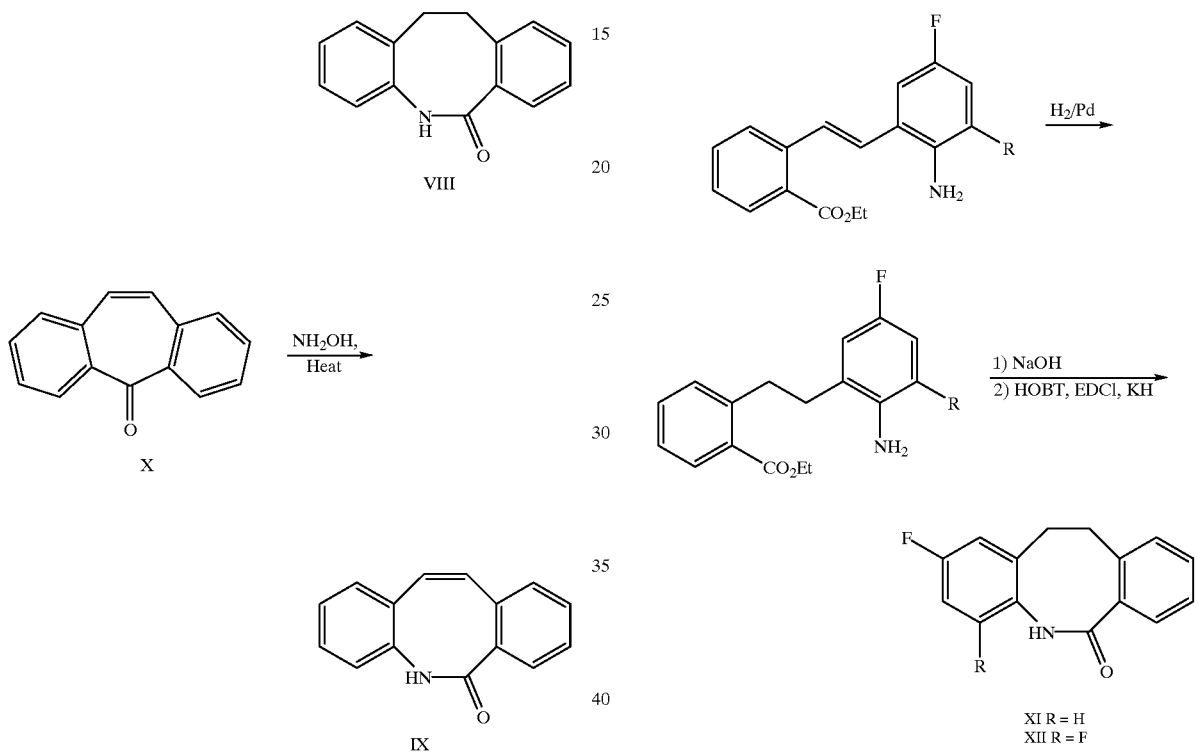

As depicted in Scheme 3, other dibenzolactam and heteroarylenediyl derivatives can be prepared via a three-step sequence: (I) palladium-catalyzed Heck reaction; (ii) hydrogenation and (iii) cyclization induced by 1-hydroxybenzotriazole hydrate (HOBT), 1-(3-dimethylaminopropyl)-3-ethylcarbodiimide hydrochloride (EDCl) and potassium hydride. For example, fluorinated derivatives XI and XII are prepared from the reaction of styryl derivative XV and anilines XIII and XIV, respectively (both purchased from Lancaster). Heteroaryl starting materials related to XV can also be prepared using the Heck reaction on the corresponding heteroaryl bromide and ethylene.

Alternatively, compound VIII can be converted to VIIIA and subsequently to VIIIB via a benzylic bromination reaction using N-bromosuccinimide (NBS) outlined in Scheme 4 and described in *J. Org. Chem.* 1972, p. 4907. This intermediate can in turn be transformed to VIIIC using standard procedures and VIIIE can be obtained from VIIIC following one of many protocol for carbonyl transposition (PhCHO,OH-/LiAlH$_4$, AlCl$_3$/O$_3$). These isomers can then each be transformed to the difluoro analog VIIID and VIIIF by reaction with DAST (diethylaminosulfur trifluoride). The lactams corresponding to products VIIID and VIIIF can then be obtained using standard hydrolytic procedures. Other lactams described herein can be prepared according to published procedures and/or are commercially available.

SCHEME 4

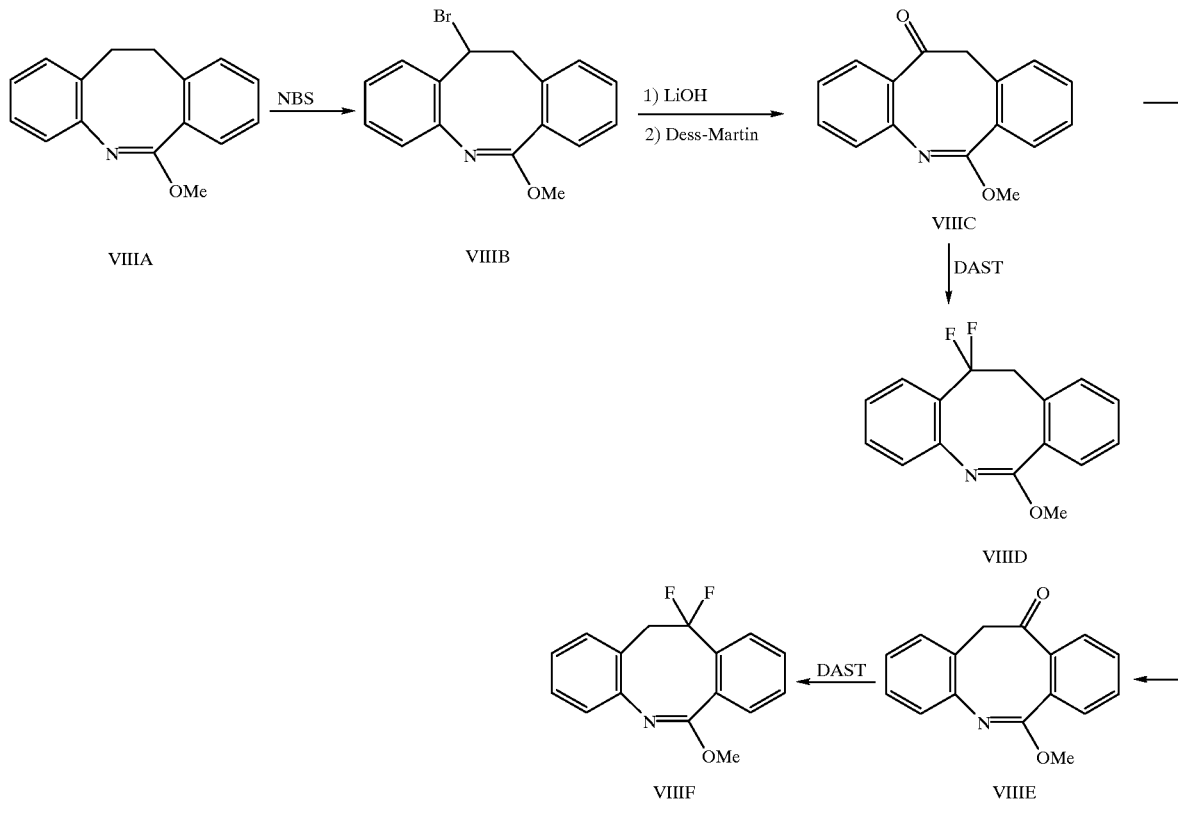

As shown in Scheme 5, dibenzolactam VIII was then treated with sodium hydride and sulfonamide VII to provide biphenyl derivative XVI which serves as a common intermediate for the synthesis of several of the compounds of the present invention. Alternatively, dibenzolactam VIII can be replaced by any of the lactams IX, XI or XII and reacted with VII. Compound XVI can then be transformed to several compounds depending on the choice of the acid chlorides used. For example, treatment of XVI with hydrocinnamoyl chloride and Hunig's base in DMF (dimethylformamide) provides acid sulfonamide XVII.

SCHEME 5

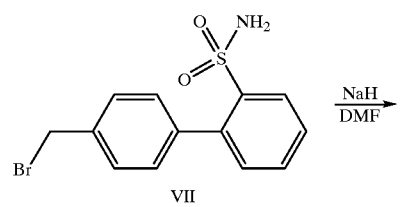

-continued

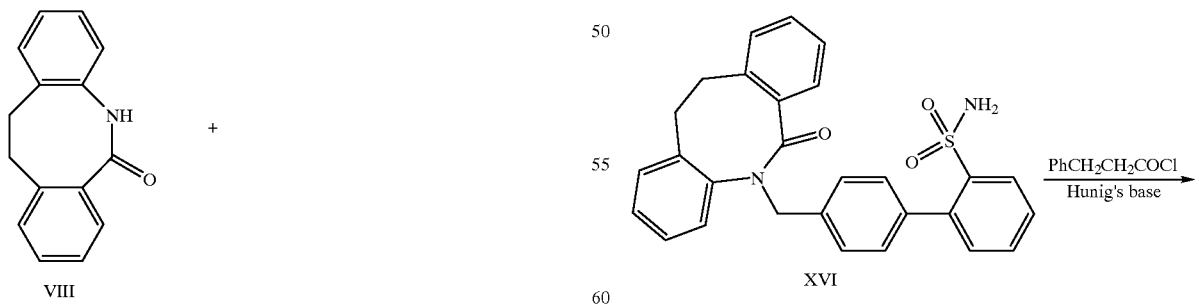

17

-continued

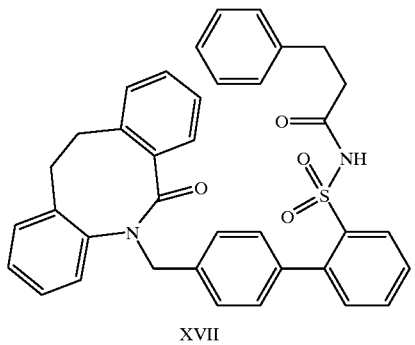

XVII

Preparation of Intermediates
2-bromo tert-butylbenzenesulfonamide IV

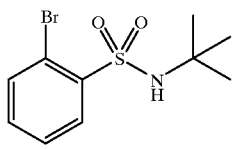

Tert-butylamine (30 mL, 0.29 mol) was slowly added to a solution of 2-bromobenzenesulfonyl chloride (30 g, 0.11 mol) with mechanical stirring at room temperature. After four hours, the precipitate was filtered and the solvent was evaporated to afford the sulfonamide.

$^1$H nmr (400 MHz, CDCl$_3$) δ ppm 8.15 (1H, dd, J=10.5, 2.0 Hz), 7.68 (1H, dd, J=10.5, 2.0 Hz), 7.40 (1H, m), 7.31 (1H, m), 5.15 (1H, br, s), 1.18 (9H, s).

Hydroxymethyl Biphenysulfonamide VI

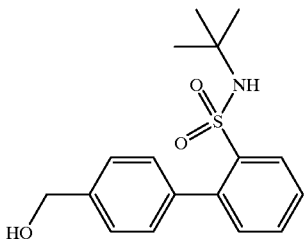

A degassed solution of 2-bromo tert-butylbenzenesulfonamide (IV) (15.6 g, 53.5 mmol) and tetrakis(triphenylphosphine)palladium (3.1 g, 2.7 mmol) in dimethoxyethane (270 mL) was stirred at room temperature for 5 minutes. Boronic acid V (purchased from Omega Chemical Company Inc.) (10 g, 53.5 mmol) and a 2M solution of sodium bicarbonate (53 mL) were then added and the mixture was heated to 90° C. and stirred at this temperature for 24 hours. The mixture was then cooled down and a saturated solution of ammonium chloride (300 mL) and ethyl acetate (300 mL) were added. The separated aqueous layer was extracted with ethyl acetate (3×100 mL) and the combined organic layers were dried (MgSO$_4$ anh.), filtered and evaporated. Flash chromatography of the residue (EtOAc-hexanes 1:1) yielded biphenyl compound VI.

$^1$H nmr (400 MHz, CDCl$_3$) δ ppm 8.15 (1H, dd, J=10.5, 2.0 Hz), 7.50 (6H, m), 7.30 (1H, m), 4.72 (2H, m), 3.61 (1H, m), 1.91 (1H, m), 1.00 (9H, s).

18

Bromomethyl Biphenyl Derivative VII

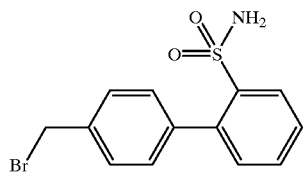

Compound VII can be prepared according to the following two alternative methods:

Method 1

A solution of hydrobromic acid (48%, 75 mL) was added to a solution of alcohol VI (22.3 g, 69.8 mmol) in acetic acid (75 mL) at room temperature. The mixture was heated to 110° C. and stirred at this temperature for 2.5 hours. After cooling to room temperature, ethanol (100 mL) and toluene (100 mL) were added and the resulting mixture was evaporated under reduced pressure. The residue was dissolved in ethyl acetate and neutralized with saturated aqueous NaHCO$_3$. The separated aqueous layer was washed with brine, dried (MgSO$_4$), filtered and evaporated.

Alternatively, compound VII was prepared according to the following two-step procedure.

Method 2

At 0° C., carbon tetrabromide (12.5 g, 37.6 mmol) was added to compound VI (10 g, 31.3 mmol) in dichloromethane (100 mL). Bis(diphenylphosphino)ethane (7.5 g, 0.6 mmol) was then added portionwise. The mixture was stirred at 0° C. for 12 hours and it was then poured into dry ether (750 mL), filtered over Celite and evaporated. Trifluoroacetic acid (100 mL) was then added and the resulting mixture was evaporated under reduced pressure. The residue was recrystallized from hexanes.

Assays For Determining Biological Activity

The compound of Formula II can be tested using the following assays to determine their prostanoid antagonist or agonist activity in vitro and in vivo and their selectivity. The prostaglandin receptors investigated were DP, EP$_1$, EP$_2$, EP$_3$, EP$_4$, FP, IP and TP.

Stable Expression of Prostanoid Receptors in the Human Embryonic Kidney (HEK) 293(ebna) Cell Line Prostanoid receptor cDNAs corresponding to full length coding sequences were subcloned into the appropriate sites of mammalian expression vectors and transfected into HEK 293(ebna) cells. HEK 293(ebna) cells expressing the individual cDNAs were grown under selection and individual colonies were isolated after 2–3 weeks of growth using the cloning ring method and subsequently expanded into clonal cell lines.

Prostanoid Receptor Binding Assays

HEK 293(ebna) cells are maintained in culture, harvested and membranes are prepared by differential centrifugation, following lysis of the cells in the presence of protease inhibitors, for use in receptor binding assays. Prostanoid receptor binding assays are performed in 10 mM MES/KOH (pH 6.0) (EPs, FP and TP) or 10 mM HEPES/KOH (pH 7.4) (DP and IP), containing 1 mM EDTA, 10 mM divalent cation and the appropriate radioligand. The reaction is initiated by addition of membrane protein. Ligands are added in dimethylsulfoxide which is kept constant at 1% (v/v) in all incubations. Non-specific binding is determined in the presence of 1 μM of the corresponding non-radioactive prostanoid. Incubations are conducted for 60 min at room temperature or 30° C. and terminated by rapid filtration. Specific binding is calculated by subtracting non specific binding from total binding. The residual specific binding at each ligand concentration is calculated and expressed as a function of ligand concentration in order to construct sigmoidal concentration-response curves for determination of ligand affinity.

Prostanoid Receptor Agonist and Antagonist Assays

Whole cell second messenger assays measuring stimulation ($EP_2$, $EP_4$, DP and IP in HEK 293(ebna) cells) or inhibition ($EP_3$ in human erythroleukemia (HEL) cells) of intracellular cAMP accumulation or mobilization of intracellular calcium ($EP_1$, FP and TP in HEK 293(ebna) cells stably transfected with apo-aequorin) are performed to determine whether receptor ligands are agonists or antagonists. For cAMP assays, cells are harvested and resuspended in HBSS containing 25 mM HEPES, pH 7.4. Incubations contain 100 $\mu$M RO-20174 (phosphodiesterase type IV inhibitor, available from Biomol) and, in the case of the $EP_3$ inhibition assay only, 15 $\mu$M forskolin to stimulate cAMP production. Samples are incubated at 37° C. for 10 min, the reaction is terminated and cAMP levels are then measured. For calcium mobilization assays, cells are charged with the co-factors reduced glutathione and coelenterazine, harvested and resuspended in Ham's F12 medium. Calcium mobilization is measured by monitoring luminescence provoked by calcium binding to the intracellular photoprotein aequorin. Ligands are added in dimethylsulfoxide which is kept constant at 1% (v/v) in all incubations. For agonists, second messenger responses are expressed as a function of ligand concentration and both $EC_{50}$ values and the maximum response as compared to a prostanoid standard are calculated. For antagonists, the ability of a ligand to inhibit an agonist response is determined by Schild analysis and both KB and slope values are calculated.

Rat Paw Edema Assay

The method is the same as described in Chan et al. (J. Pharmacol. Exp. Ther. 274: 1531–1537, 1995).

LPS-Induced Pyrexia in Conscious Rats

The method is the same as described in Chan et al. (J. Pharmacol. Exp. Ther. 274: 1531–1537, 1995).

LPS-Induced Pyrexia in Conscious Squirrel Monkeys

The method is the same as described in Chan et al. (Eur. J. Pharmacol. 327: 221–225, 1997).

Acute Inflammatory Hyperalgesia Induced by Carrageenan in Rats

The method is the same as described in Boyce et al. (Neuropharmacology 33: 1609–1611, 1994).

Adjuvant-Induced Arthritis in Rats

Female Lewis rats (body weight ~146–170 g) were weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10–3.0 mg/kg) such that the body weights were equivalent within each group. Six groups of 10 rats each were injected into a hind paw with 0.5 mg of *Mycobacterium butyricum* in 0.1 mL of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) were determined before (day −1) and 21 days following adjuvant injection, and primary paw volumes were determined before (day −1) and on days 4 and 21 following adjuvant injection. The rats were anesthetized with an intramuscular injection of 0.03–0.1 mL of a combination of Ketamine (87 mg/kg) and Xylazine (13 mg/kg) for radiographs and injection of adjuvant. The radiographs were made of both hind paws on day 0 and day 21 using the Faxitron (45 kVp, 30 seconds) and Kodak X-OMAT TL film, and were developed in an automatic processor. Radiographs were evaluated for changes in the soft and hard tissues by an investigator who was blinded to experimental treatment. The following radiographic changes were graded numerically according to severity: increased soft issue volume (0–4), narrowing or widening of joint spaces (0–5) subehondral erosion (0–3), periosteal reaction (0–4), osteolysis (0–4) subluxation (0–3), and degenerative joint changes (0–3). Specific criteria were used to establish the numerical grade of severity for each radiographic change. The maximum possible score per foot was 26. A test compound at total daily doses of 0.1, 0.3, 1, and 3 mg/kg/day, indomethacin at a total daily dose of 1 mg/kg/day, or vehicle (0.5% methocel in sterile water) were administered per os b.i.d. beginning post injection of adjuvant and continuing for 21 days. The compounds were prepared weekly, refrigerated in the dark until used, and vortex mixed immediately prior to administration.

The invention is illustrated in the following non-limiting Examples in which, unless otherwise stated:

(i) all the end products of the formula II were analyzed by NMR, TLC and mass spectrometry;

(ii) intermediates were analyzed by NMR and TLC;

(iii) most compounds were purified by flash chromatography on silica gel, recrystallization and/or swish (suspension in a solvent followed by filtration of the solid) with a solvent such as ether:hexane 1:1;

(iv) the course of reactions was followed by thin layer chromatography (TLC) and reaction times are given for illustration only;

(v) temperatures are in degrees Celsius.

Table I illustrates compounds of formula II which are representative of the present invention.

TABLE 1

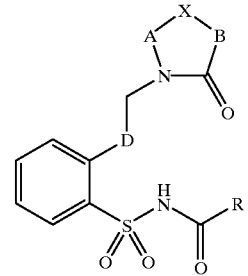

| EX. | A | B | D | X | R |
|---|---|---|---|---|---|
| 1 | 1,2-Ph | 1,2-Ph | 1,4-Ph | $CH_2CH_2$ | $CH_2CH_2Ph$ |
| 2 | 1,2-Ph | 1,2-Ph | 1,4-Ph | $CH_2CH_2$ | $NH(CH_2)_2Ph$ |
| 3 | 1,2-Ph | 1,2-Ph | 1,4-Ph | $CH_2CH_2$ | $NH(CH_2)_3Ph$ |
| 4 | 1,2-Ph | 1,2-Ph | 1,4-Ph | $CH_2CH_2$ | $OCH_2Ph$ |
| 5 | 1,2-Ph | 1,2-Ph | 1,4-Ph | $CH_2CH_2$ | $CH_2OPh$ |
| 6 | 1,2-Ph | 1,2-Ph | 1,4-Ph | $CH_2CH_2$ | $CH_2Ph$ |
| 7 | 1,2-Ph | 1,2-Ph | 1,4-Ph | $CH_2CH_2$ | $C(CH_3)_2Ph$ |
| 8 | 1,2-Ph | 1,2-Ph | 1,4-Ph | $CH_2CH_2$ | $CH(CH_3)Ph$ |
| 9 | 1,2-Ph | 1,2-Ph | 1,4-Ph | $CH_2CH_2$ | $C(CH_3)_2CH_2Ph$ |
| 10 | 1,2-Ph | 1,2-Ph | 1,4-Ph | CH=CH | $C(CH_3)_2CH_2Ph$ |
| 11 | 4-F,1,2-Ph | 1,2-Ph | 1,4-Ph | $CH_2CH_2$ | $C(CH_3)_2CH_2Ph$ |
| 12 | 4,6-F,1,2-Ph | 1,2-Ph | 1,4-Ph | $CH_2CH_2$ | $C(CH_3)_2CH_2Ph$ |
| 13 | 1,2-Ph | 1,2-Ph | 1,4-Ph | $CH_2CH_2$ | (S)—$C(CF_3)(OCH_3)Ph$ |
| 14 | 1,2-Ph | 1,2-Ph | 1,4-Ph | $CH_2CH_2$ | (R)—$C(CF_3)(OCH_3)Ph$ |
| 15 | 1,2-Ph | 1,2-Ph | 1,4-Ph | $CH_2CH_2$ | $NCH_3(CH_2)_2Ph$ |
| 16 | 1,2-Ph | 1,2-Ph | 1,4-Ph | $CH_2CH_2$ | (S)—$NHCH(CH_3)Ph$ |
| 17 | 1,2-Ph | 1,2-Ph | 1,4-Ph | $CH_2CH_2$ | $NH(CH_2)_2$-2-Thiophene |
| 18 | 1,2-Ph | 1,2-Ph | 1,4-Ph | $CH_2CH_2$ | (E)—CH=CHPh |
| 19 | 1,2-Ph | 1,2-Ph | 1,4-Ph | $CH_2CH_2$ | $NH(CH_2)_3CH_3$ |
| 20 | 5-Cl, 1,2-Ph | 1,2-Ph | 1,4-Ph | $OCH_2$ | $NH(CH_2)_2$-2-Thiophene |
| 21 | 1,2-Ph | 1,2-Ph | 1,4-Ph | $CH_2CH_2$ | $NHC(CH_3)_3$ |
| 22 | 1,2-Ph | 1,2-Ph | 1,4-Ph | $CH_2CH_2$ | $NHCH_2Ph$ |

TABLE 1-continued

[Structure shown with substituents A, B, D, X, R]

| EX. | A | B | D | X | R |
|---|---|---|---|---|---|
| 23 | 1,2-Ph | 1,2-Ph | 1,4-Ph | CH$_2$CH$_2$ | o-Cl-Ph |
| 24 | 1,2-Ph | 1,2-Ph | 1,4-Ph | OCH$_2$ | NH(CH$_2$)$_2$2-Thiophene |

EXAMPLE 1

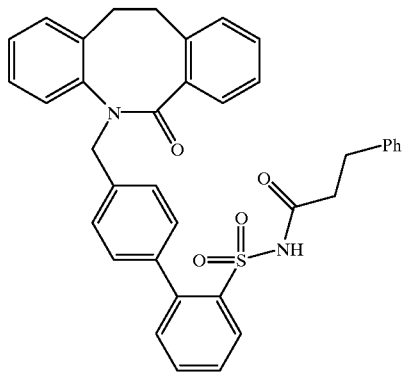

$^1$H nmr (400 MHz, CDCl$_3$) δ ppm 8.22 (1H, d, J=10.5), 7.70 (1H, t, J=10.5 Hz), 7.61 (1H, t, J=10.5 Hz), 7.35–6.85 (18H, m), 5.70 (1H, m), 5.21 (1H, d, J=18.0 Hz), 4.90 (1H, d, J=18.0 Hz), 3.40, 3.25, 2.85 (4H, 3 m), 2.97 (2H, t, J=7.0 Hz), 2.45 (2H, t, J=7.0 Hz). Elemental analysis calculated for C$_{37}$H$_{31}$N$_2$NaSO$_4$.2H$_2$O:C, 67.46; H, 5.36; N, 4.25: found: C, 67.48; H, 4.72; N, 3.57.

EXAMPLE 2

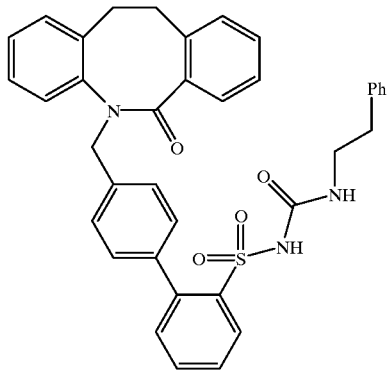

$^1$H nmr (400 MHz, CDCl$_3$) δ ppm 8.18 (1H, d, J=10.5), 7.66 (1H, t, J=10.5 Hz), 7.59 (1H, t, J=10.5 Hz), 7.35–6.91 (19H), 6.12 (1H, m), 5.30 (1H, d, J=18.0 Hz), 4.85 (1H, d, J=18.0 Hz), 3.30 (3H, m), 2.85 (5H, m). Elemental analysis calculated for C$_{37}$H$_{32}$N$_3$NaSO$_4$.2H$_2$O:C, 65.96; H, 5.39; N, 6.24: found: C, 66.28; H, 5.04; N, 6.23.

EXAMPLE 3

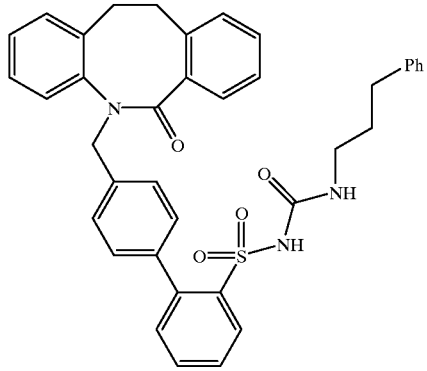

$^1$H nmr (400 MHz, CDCl$_3$) δ ppm 8.18 (1H, d, J=10.5), 7.70 (1H, t, J=10.5 Hz), 7.60 (1H, t, J=10.5 Hz), 7.38–6.95 (19H), 6.15 (1H, m), 5.28 (1H, d, J=18.0 Hz), 4.88 (1H, d, J=18.0 Hz), 3.30–2.50 (8H, m), 1.70 (2H, m). Elemental analysis calculated for C$_{38}$H$_{34}$N$_3$NaSO$_4$.1.5H$_2$O:C, 67.24; H, 5.49; N, 6.19: found: C, 67.49; H, 5.38; N, 6.14.

EXAMPLE 4

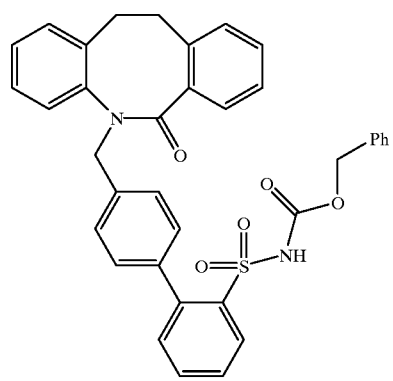

$^1$H nmr (400 MHz, CD$_3$COCD$_3$) δ ppm 8.19 (1H, d, J=10.5 Hz), 7.69 (1H, t, J=10.5 Hz), 7.59 (1H, t, J=10.5 Hz), 7.35–6.90 (18H), 5.27 (1H, d, J=10.0 Hz), 5.02 (2H, s), 4.87 (1H, d, J=10.0 Hz), 3.25 (1H, m), 2.80 (3H, m). Elemental analysis calculated for C$_{36}$H$_{29}$N$_2$NaSO$_5$.3H$_2$O:C, 63.70; H, 5.20; N, 4.13: found: C, 63.51; H, 5.20; N, 4.13.

EXAMPLE 5

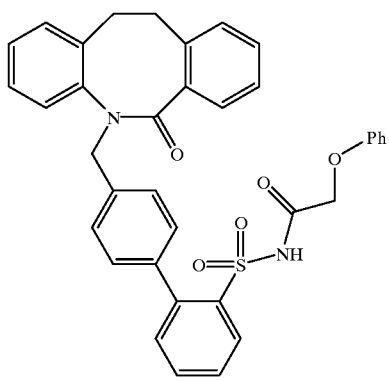

1H nmr (400 MHz, CD$_3$COCD$_3$) δ ppm 8.21 (1H, d, J=10.5 Hz), 7.75 (1H, t, J=10.5 Hz), 7.68 (1H, t, J=10.5 Hz), 7.38–6.86 (19H), 5.22 (1H, d, J=10.0 Hz), 4.80 (1H, J=10.0 Hz), 4.50 (2H, s), 3.22 (1H, m), 2.80 (3H, m). Elemental analysis calculated for C$_{36}$H$_{29}$N$_2$NaSO$_5$.1.5H$_2$O:C, 66.35; H, 4.95; N, 4.30: found: C, 66.03; H, 4.62; N, 4.20.

EXAMPLE 6

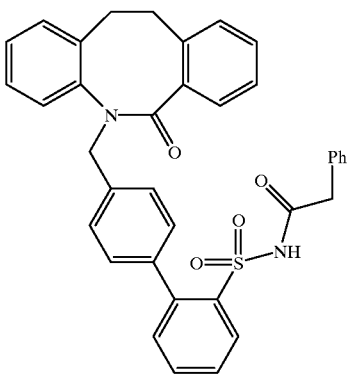

1H nmr (400 MHz, CD$_3$COCD$_3$) δ ppm 8.20 (1H, d, J=10.5), 7.70 (1H, t, J=10.5 Hz), 7.60 (1H, t, J=10.5 Hz), 7.35–6.90 (18H), 5.25 (1H, d, J=18.0 Hz), 5.02 (2H, s), 4.95 (1H, d, J=18.0 Hz), 3.50 (2H, s), 3.28 (1H, m), 2.80 (3H, m). Elemental analysis calculated for C$_{36}$H$_{29}$N$_2$NaSO$_4$.2H$_2$O:C, 67.07; H, 5.16; N, 4.34: found: C, 67.36; H, 4.85; N, 4.21.

EXAMPLE 7

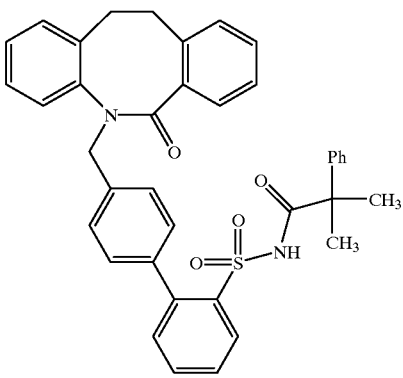

1H nmr (400 MHz, CDCl$_3$) δ ppm 8.32 (dd, J=7.9, 1.5 Hz, 1H), 7.62 (dt, J=7.5, 1.4Hz, 1H), 7.55 (dt, J=7.5, 1.5 Hz, 1H), 7.33–6.86 (m, 19H), 5.33 (d, J=13.8 Hz, 1H), 4.68 (d, J=13.8 Hz, 1H), 3.22 (m, 1H), 2.77 (m, 1H), 2.62 (m, 2H), 1.47 (s, 6H).

EXAMPLE 8

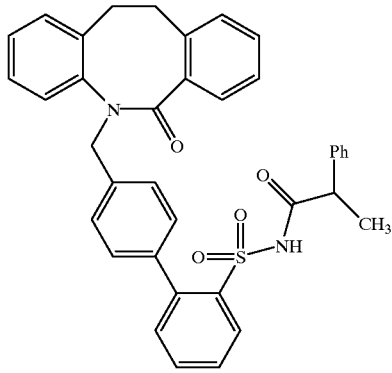

$^1$H nmr (400 MHz, CDCl$_3$) δ ppm 8.32 (d, J=8.0 Hz, 1H), 7.57 (t, J=7.5, 1H), 7.50 (t, J=7.8 Hz, 1H), 7.30–6.87 (m, 18H), 5.13 (dd, J=13.9, 2.3 Hz, 1H), 4.54 (dd, J=30.9, 14.0 Hz, 1H), 3.43 (m, 1H), 3.28 (m, 1H), 2.82 (m, 1H), 2.65 (m, 2H), 1.30 (d, J=7.0 Hz, 3H). Elemental analysis calculated for C$_{37}$H$_{36}$N$_2$NaSO$_4$.1.5H$_2$O: C, 68.39; H, 5.27; N, 4.31; S, 4.93: found: C, 68.26; H, 5.22; N, 4.32; S, 4.65.

EXAMPLE 9

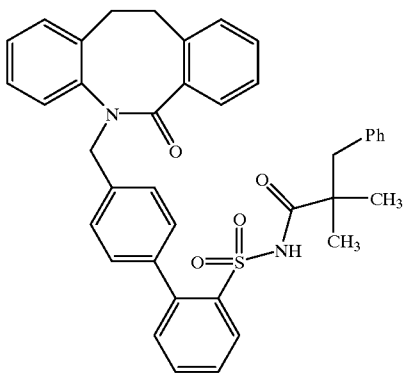

$^1$H nmr (400 MHz, CDCl$_3$) δ ppm 8.34 (dd, J=7.8, 1.1 Hz, 1H), 7.64 (dt, J=7.5, 1.4Hz, 1H), 7.57 (dt, J=7.6, 1.4Hz, 1H), 7.24–6.84 (m, 19H), 5.25 (d, J=13.0 Hz, 1H), 4.75 (d, J=14.0 Hz, 1H), 3.27 (m, 1H), 2.69 (s, 2H), 2.85–2.60 (m, 3H), 0.99 (s, 3H), 0.98 (s, 3H). Elemental analysis calculated for C$_{39}$H$_{35}$N$_2$NaSO$_4$.2H$_2$O:C, 68.20; H, 5.72; N, 4.08: found: C, 68.17; H, 5.68; N, 3.95.

EXAMPLE 10

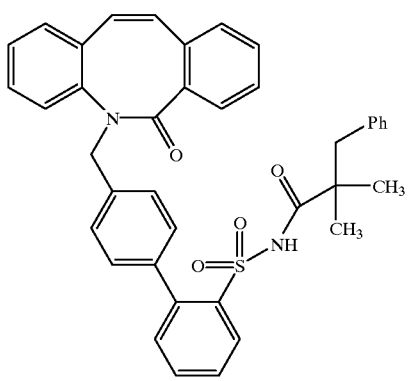

$^1$H nmr (400 MHz, CDCl$_3$) δ ppm 8.36 (dd, J=7.9, 1.1 Hz, 1H), 7.64 (dt, J=7.5, 1.4 Hz, 1H), 7.57 (dt, J=7.8, 1.4 Hz, 1H), 7.43–6.88 (m, 18H), 6.83 (d, J=11.5 Hz, 1H), 6.51 (d, J=11.5 Hz, 1H), 5.52 (d, J=14.4 Hz, 1H), 4.46 (d, J=14.4 Hz, 1H), 2.69 (m, 2H), 0.98 (s, 3H), 0.96 (s, 3H). Elemental analysis calculated for C$_{39}$H$_{33}$N$_2$NaSO$_4$.3H$_2$O:C, 66.65; H, 5.59; N, 3.98: found: C, 66.80; H, 5.08; N, 4.02.

EXAMPLE 11

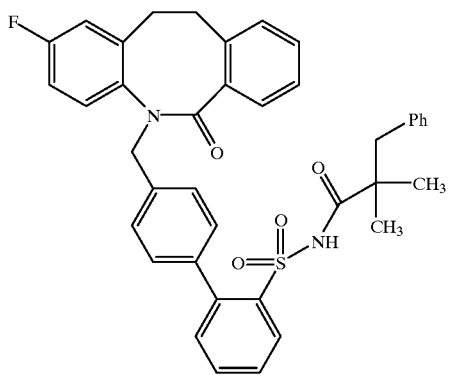

$^1$H nmr (400 MHz, CD$_3$COCD$_3$) δ ppm 8.35 (dd, J=7.9, 1.2 Hz, 1H), 7.66 (dt, J=7.4, 1.3 Hz, 1H), 7.59 (dt, J=7.8, 1.3 Hz, 1H), 7.37–6.62 (m, 17H), 5.24 (d, J=14.0 Hz, 1H), 4.71 (d, J=14.0 Hz, 1H), 3.27 (m, 1H), 2.70 (s, 2H), 2.85–2.56 (m, 3H), 1.01 (s, 3H), 1.00 (s, 3H). Elemental analysis calculated for C$_{39}$H$_{34}$N$_2$NaFSO$_4$.2.5H$_2$O:C, 65.62; H, 5.51; N, 3.92: found: C, 65.37; H, 5.35; N, 3.95.

EXAMPLE 12

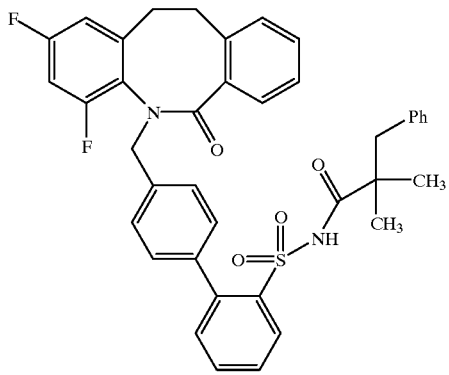

$^1$H nmr (400 MHz, CD$_3$COCD$_3$) δ ppm 8.28 (1H, d, J=10.5), 7.71 (1H, t, J=10.5 Hz), 7.63 (1H, t, J=10.5 Hz), 7.31–6.60 (17H), 5.77 (1H, d, J=20.0 Hz), 4.22 (1H, d, J=20.0 Hz), 3.50 (2H, s), 3.18 (1H, m), 2.85, (1H, m), 2.70 (1H, m), 2.55 (1H, 3m). Elemental analysis calculated for C$_{39}$H$_{33}$N$_2$NaF$_2$SO$_4$.2H$_2$O:C, 64.81; H, 5.16; N, 5.26: found: C, 36.1; H, 2.90; N, 1.91.

EXAMPLE 13

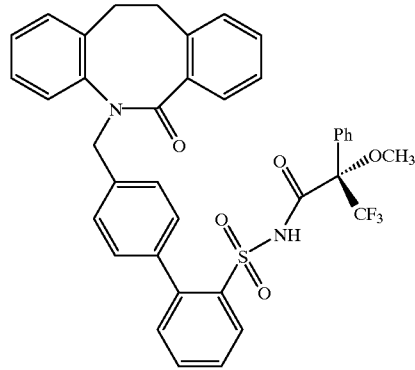

$^1$H nmr (400 MHz, CDCl$_3$) δ ppm 8.60 (bs, 1H), 8.29 (d, J =8.0 Hz, 1H), 7.62 (t, J=7.5 Hz, 1H), 7.50 (t, J=7.8 Hz, 1H), 7.40–6.86 (m, 18H), 5.33 (dd, J=13.9, 5.9 Hz, 1H), 4.74 (dd, J=13.8, 5.8 Hz, 1H), 3.38 (s, 3H), 3.28 (m, 1H), 2.83 (m, 1H), 2.69 (m, 2H). Elemental analysis calculated for C$_3$sH$_{30}$N$_2$NaF$_3$SO$_5$.2.5H$_2$O:C, 60.71; H, 4.69; N, 3.73: found: C, 60.63; H, 4.17; N, 3.48.

EXAMPLE 14

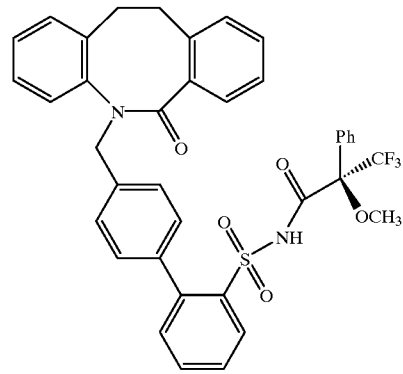

$^1$H nmr (400 MHz, CDCl$_3$) δ ppm 8.45 (bs, 1H), 8.33 (dd, J=8.0, 1.3 Hz, 1H), 7.66 (dt, J=7.5, 1.4 Hz, 1H), 7.57 (dt, J=7.9, 1.4 Hz, 1H), 7.44–6.88 (m, 18H), 5.35 (dd, J=13.9, 4.9 Hz, 1H), 4.78 (dd, J=13.9, 3.8 Hz, 1H), 3.41 (t, J=1.5 Hz, 3H), 3.29 (m, 1H), 2.84 (m, 1H), 2.71 (m, 2H). Elemental analysis calculated for C$_{38}$H$_{30}$N$_2$NaF$_3$SO$_5$.2.5H$_2$O:C, 60.71; H, 4.69; N, 3.73: found: C, 60.43; H, 4.29; N, 3.76.

EXAMPLE 15

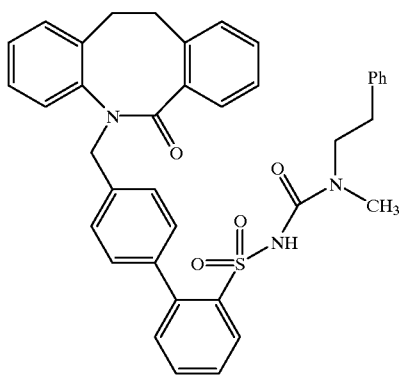

¹H nmr (400 MHz, CD₃COCD₃) δ ppm 8.17 (d, J=8.0, 1H), 7.65 (t, J=7.5, Hz, 1H), 7.59 (t, J=7.6, 1H), 7.38 (d, J=8.5 Hz, 2H), 7.35–7.05 (m, 16H), 6.9 (d, J=8.0 Hz, 1H), 5.21 (d, J=15.0 Hz, 1H), 4.92 (d, J=15.0 Hz, 1H), 3.41 (t, J=7.0 Hz, 2H), 3.29 (m, 1H), 2.84 (m, 5H). Elemental analysis calculated for $C_{38}H_{34}N_3NaSO_4 \cdot 2.5H_2O$: C, 65.50; H, 5.61; N, 6.03; S, 4.60: found: C, 65.64; H, 5.48; N, 5.70; S, 4.62.

EXAMPLE 16

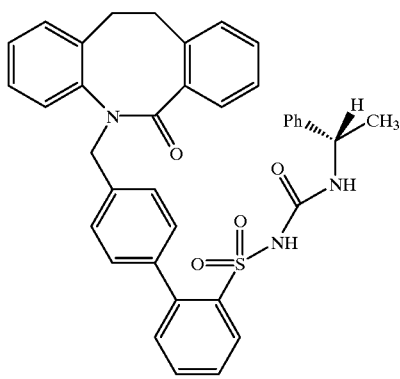

¹H nmr (400 MHz, CD₃COCD₃) δ ppm 8.18 (d, J=8.0 Hz, 1H), 7.67 (t, J=7.5, Hz, 1H), 7.56 (t, J=7.6, 1H), 7.35–6.92 (19H), 6.40, 5.70 (2m, NH rotamers), 5.28 (m, 1H), 4.80 (m, 2H), 3.27 (m, 1H), 2.85 (m, 3H), 1.35 (2d-rotamers, J=7.0 Hz, 3H). Elemental analysis calculated for $C_{37}H_{32}N_3NaSO_4 \cdot 5H_2O$: C, 61.06; H, 5.81; N, 5.77: found: C, 61.94; H, 5.03; N, 6.03.

EXAMPLE 17

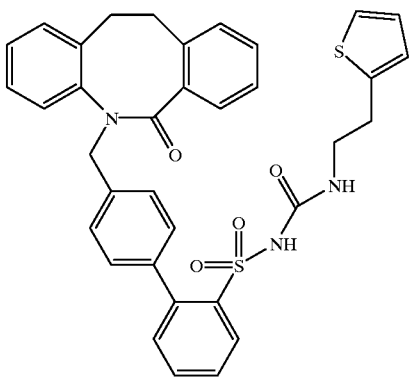

¹H nmr (400 MHz, CD₃COCD₃) δ ppm 8.19 (d, J=8.0 Hz, 1H), 7.70 (t, J=7.5, Hz, 1H), 7.59 (t, J=7.6, 1H), 7.37–6.70 (17H), 6.18 (br, s, 1H), 5.30 (d, J=10.0 Hz, 1H), 4.78 (d, J=10.0 Hz, 1H), 3.38 (m, 3H), 2.90 (m, 5H). Elemental analysis calculated for $C_{35}H_{30}N_3NaS_2O_4 \cdot 2H_2O$: C, 61.84; H, 5.04; N, 6.18; S, 9.43: found: C, 61.59; H, 4.78; N, 6.09; S, 9.51.

EXAMPLE 18

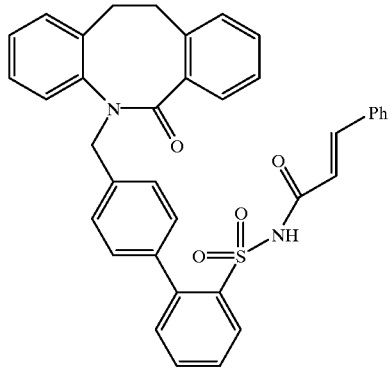

¹H nmr (400 MHz, CD₃COCD₃) δ ppm 8.30 (d, J=8.0 Hz, 1H), 7.71 (t, J=7.5, Hz, 1H), 7.65 (t, J=7.6, 1H), 7.60–6.90 (19H), 7.08 (d, J=15.0 Hz, 1H), 6.57 (d, J=15.0 Hz, 1H), 5.23 (d, J=12.0 Hz, 1H), 4.91 (d, J=12.0 Hz, 1H), 3.29 (m, 1H), 2.88 (m, 2H), 2.76 (m, 1H). Elemental analysis calculated for $C_{37}H_{29}N_2NaSO_4 \cdot 1.5H_2O$: C, 68.61; H, 4.98; N, 4.32; S, 4.95: found: C, 68.47; H, 4.81; N, 4.37; S, 4.30.

EXAMPLE 19

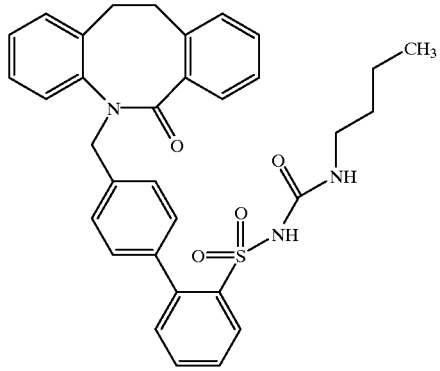

¹H nmr (400 MHz, CDCl₃) δ ppm 8.20 (d, J=8.0 Hz, 1H), 7.70 (t, J=7.5, Hz, 1H), 7.61 (t, J=7.6, 1H), 7.40–6.92 (13H), 5.31 (d, J=10.5 Hz, 1H), 4.89 (d, J=10.5 Hz, 1H), 3.32–2.70 (m, 6H), 1.30 (m, 4H), 0.85 (t, J=7.0 Hz, 3H). Elemental analysis calculated for $C_{33}H_{32}N_3NaSO_4 \cdot H_2O$: C, 65.22; H, 5.64; N, 6.91; found: C, 65.24; H, 5.64; N, 6.82.

EXAMPLE 20

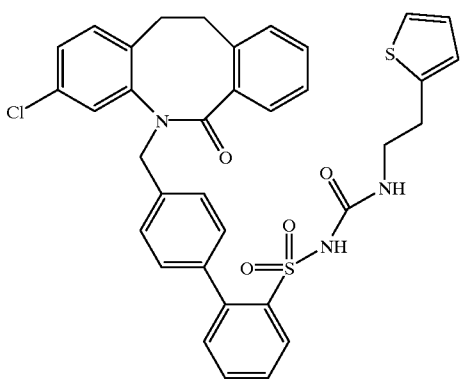

$^1$H nmr (400 MHz, CD$_3$COCD$_3$) 2 rotamers (2:1) δ ppm 8.16, 8.11 (d, J=8.0 Hz, 1H), 7.90–6.70 (17H), 6.88, 6.70 (m, 1H), 5.50, 5.46 (s, 2H), 3.30 (m, 2H), 2.91 (m, 2H). Elemental analysis calculated for C$_{33}$H$_{25}$N$_3$NaS$_2$ClO$_5$.2H$_2$O:C, 56.45; H, 4.16; N, 5.98; found: C, 56.60; H, 3.86; N, 5.68.

EXAMPLE 21

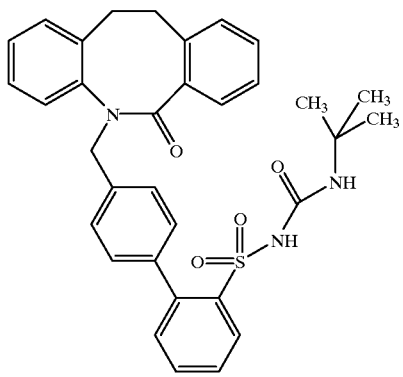

$^1$H nmr (400 MHz, CD$_3$COCD$_3$) δ ppm 8.20 (d, J=8.0 Hz, 1H), 7.79 (t, J=8.0 Hz, 1H), 7.60 (t, J=8.0 Hz, 1H), 7.40–6.95 (m, 13H), 5.92 (s, 1H), 5.30 (d, J=10.0 Hz), 4.90 (d, J=10.0 Hz), 3.29 (m, 1H), 2.85 (m, 3H). Elemental analysis calculated for C$_{33}$H$_{32}$N$_3$NaSO$_4$.2H$_2$O:C, 63.34; H, 5.80; N, 6.72; found: C, 63.84; H, 5.43; N, 6.50.

EXAMPLE 22

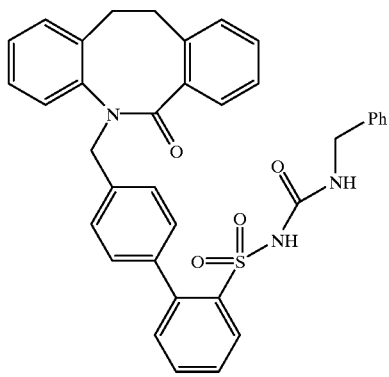

$^1$H nmr (400 MHz, CD$_3$COCD$_3$) δ ppm 8.19 (d, J=8.0 Hz, 1H), 7.79 (t, J=8.0 Hz, 1H), 7.58 (t, J=8.0 Hz, 1H), 7.35–6.90 (m, 18H), 6.53 (br, t, J=7.0 Hz, 2H), 5.29 (d, J=12.5 Hz), 4.82 (d, J=12.5 Hz), 4.21 (d, J=7.0 Hz), 3.25 (m, 1H), 2.80 (m, 3H). Elemental analysis calculated for C$_{36}$H$_{30}$N$_3$NaSO$_4$.1.5H$_2$O:C, 66.45; H, 5.11; N, 6.46; found: C, 66.47; H, 4.91; N, 6.40.

EXAMPLE 23

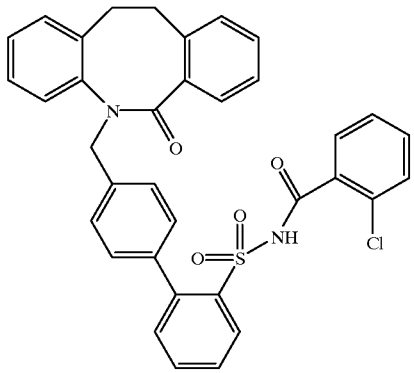

$^1$H nmr (400 MHz, CD$_3$COCD$_3$) δ ppm 8.35 (d, J=8.0 Hz, 1H), 7.75 (t, J=8.0 Hz, 1H), 7.59 (t, J=8.0 Hz, 1H), 7.45–6.91 (m, 18H), 5.21 (d, J=10.0 Hz), 4.87 (d, J=10.0 Hz), 3.21 (m, 1H), 2.80 (m, 3H). Elemental analysis calculated for C$_{35}$H$_{26}$N$_2$NaClSO$_4$.2H$_2$O:C, 63.20; H, 4.55; N, 4.21; found: C, 63.60; H, 4.32; N, 4.13.

EXAMPLE 24

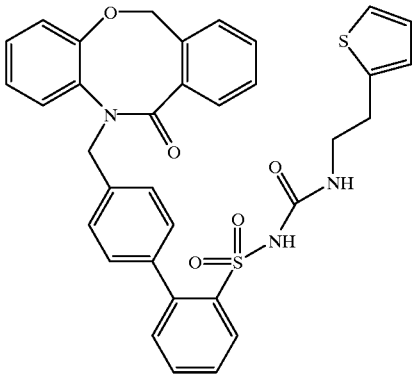

$^1$H nmr (400 MHz, CD$_3$COCD$_3$) δ ppm 8.61 (br, s, 1H), 8.17 (d, J=8.0 Hz, 1H), 7.88 (d, J=8.0 Hz, 1H), 7.69 (t, J=8.0 Hz, 1H), 7.60–7.20 (m, 16H), 6.89 (m, 1H), 6.80 (m, 1H), 6.03 (br, t, J=6.5 Hz, 1H), 5.45 (s, 2H), 3.30 (q, J=6.5 Hz, 2H), 2.91 (t, J=6.5 Hz, 2H). Elemental analysis calculated for C$_{33}$H$_{26}$N$_3$NaS$_2$O$_5$.1.5H$_2$O:C, 60.17; H, 4.44; N, 6.38; found: C, 60.42; H, 4.10; N, 6.18.

What is claimed is:

1. A compound of structural Formula II:

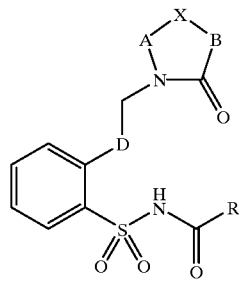

or a pharmaceutically acceptable salt, crystal form, or hydrate thereof, wherein:

A and B are independently unsubstituted, monosubstituted or disubstituted ortho-benzenediyl wherein the substituents are selected from the group consisting of:
 a) halogen,
 b) $C_{1-5}$ alkyl,
 c) $C_{1-5}$ alkoxy,
 d) $C_{1-5}$ alkylthio,
 e) nitro,
 f) CN,
 g) $C_{1-5}$ fluoroalkyl,
 h) $COOR^3$, and
 i) $NR^3{}_2$;

X is $CH_2CH_2CH=CH$, $CH_2Y$ or $YCH_2$;

Y is O;

D is unsubstituted, monosubstituted, or disubstituted benzendiyl wherein the substituents are selected from:
 a) halogen,
 b) $C_{1-5}$ alkyl,
 c) $C_{1-5}$ alkoxy,
 d) $C_{1-5}$ alkylthio,
 e) nitro,
 f) CN,
 g) $C_{1-5}$ fluoroalkyl,
 h) $COOR^3$, and
 i) $NR^3{}_2$;

R is:
 a) $C_{1-6}$ alkyl,
 b) $(CR^1R^2)_nO$—Ph,
 c) $(CR^1R^2)_n$O-heteroaryl,
 d) O—$(CR^1R^2)_n$Ph,
 e) O—$(CR^1R^2)_n$heteroaryl,
 f) $NR^3$—$(CR^1R^2)_n$Ph,
 g) $NR^3$—$(CR^1R^2)_n$heteroaryl,
 h) $C_{2-6}$ alkenyl-Ph,
 i) $C_{2-6}$ alkenyl-heteroaryl,
 j) $(CR^1R^2)_n$Ph, or
 k) $(CR^1R^2)_n$heteroaryl,
  wherein Ph or heteroaryl is unsubstituted, monosubstituted or disubstituted with substituents selected from:
   1) halogen,
   2) $C_{1-5}$ alkyl,
   3) $C_{1-5}$ alkoxy,
   4) $C_{1-5}$ alkylthio,
   5) nitro,
   6) CN,
   7) $C_{1-5}$ fluoroalkyl,
   8) $COOR^3$, and
   9) $NR^3{}_2$;

n=0, 1, 2 or 3;

$R^1$ and $R^2$ are independently hydrogen, $C_{1-3}$ alkyl, benzyl, $C_{1-3}$ fluoroalkyl, $C_{1-3}$ alkoxy, or fluorine;

$R^3$ is H or $C_{1-6}$ alkyl.

2. The compound of structural Formula II as recited in claim 1, wherein:

A and B are independently unsubstituted, monosubstituted or disubstituted ortho-benzenediyl wherein the substituents are selected from the group consisting of:
 a) halogen,
 b) $C_{1-5}$ alkyl,
 c) $C_{1-5}$ alkoxy,
 d) $C_{1-5}$ alkylthio,
 e) nitro,
 f) CN,
 g) $C_{1-5}$ fluoroalkyl,
 h) $COOR^3$, and
 i) $NR^3{}_2$;

X is $CH_2CH_2$, $CH=CH$, $CH_2Y$ or $YCH_2$;

Y is O;

D is unsubstituted or monosubstituted benzendiyl wherein the substituents are selected from:
 a) halogen,
 b) $C_{1-3}$ alkyl,
 c) $C_{1-3}$ alkoxy,
 d) $C_{1-3}$ alkylthio,
 e) nitro,
 f) CN,
 g) $C_{1-3}$ fluoroalkyl,
 h) $COOR^3$, and
 i) $NR^3{}_2$;

R is:
 a) $C_{1-6}$ alkyl,
 b) $(CR^1R^2)_nO$—Ph,
 c) O—$(CR^1R^2)_n$Ph,
 d) $NR^3$—$(CR^1R^2)_n$Ph,
 e) $NR^3$—$(CR^1R^2)_n$heteroaryl,
 f) $C_{2-6}$ alkenyl-Ph, or
 g) $(CR^1R^2)_n$Ph,
  wherein Ph or heteroaryl is unsubstituted, monosubstituted or disubstituted with substituents selected from:
   1) halogen,
   2) $C_{1-3}$ alkyl,
   3) $C_{1-3}$ alkoxy,
   4) $C_{1-3}$ alkylthio,
   5) nitro,
   6) CN,
   7) $C_{1-3}$ fluoroalkyl,
   8) $COOR^3$, and
   9) $NR^3{}_2$;

n=0, 1, 2 or 3;

$R^1$ and $R^2$ are independently hydrogen, $C_{1-3}$ alkyl, $C_{1-3}$ fluoroalkyl, or $C_{1-3}$ alkoxy;

$R^3$ is H or $C_{1-6}$ alkyl.

3. The compound of structural Formula II as recited in claim 1, wherein:

A and B are independently unsubstituted, monosubstituted or disubstituted ortho-benzenediyl wherein the substituents are halogen;

X is $CH_2CH_2$, $CH=CH$, or $OCH_2$;

D is benzendiyl;

R is:
- a) $C_{1-3}$ alkyl,
- b) $(CR^1R^2)_nO$—Ph,
- c) O—$(CR^1R^2)_n$Ph,
- d) $NR^3$—$(CR^1R^2)_n$Ph,
- e) $NR^3$—$(CR^1R^2)_n$thienyl,
- f) $C_{2-3}$ alkenyl-Ph, or
- g) $(CR^1R^2)_n$Ph,
  wherein Ph is unsubstituted or monosubstituted with halogen;

n=0, 1, 2 or 3;

$R^1$ and $R^2$ are independently hydrogen, $C_{1-3}$ alkyl, $C_{1-3}$ fluoroalkyl, or $C_{1-3}$ alkoxy;

$R^3$ is H or $C_{1-3}$ alkyl.

4. A method for treating inflammation comprising administering to a mammalian patient in need of such treatment a therapeutically effective amount of a compound according to claim 1.

5. A pharmaceutical composition comprising a pharmaceutically acceptable carrier and a compound of Formula II, as recited in claim 1, or a pharmaceutically acceptable crystal form or hydrate thereof.

6. A process for making a pharmaceutical composition comprising combining a compound of claim 1 and a pharmaceutically acceptable carrier.

7. A compound of structural Formula II:

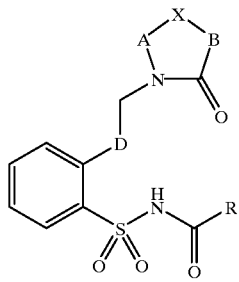

II or a pharmaceutically acceptable salt, crystal form, or hydrate thereof, wherein the substituents are defined as:

| A | B | D | X | R |
|---|---|---|---|---|
| 1,2-Ph | 1,2-Ph | 1,4-Ph | $CH_2CH_2$ | $CH_2CH_2Ph$ |
| 1,2-Ph | 1,2-Ph | 1,4-Ph | $CH_2CH_2$ | $NH(CH_2)_2Ph$ |
| 1,2-Ph | 1,2-Ph | 1,4-Ph | $CH_2CH_2$ | $NH(CH_2)_3Ph$ |
| 1,2-Ph | 1,2-Ph | 1,4-Ph | $CH_2CH_2$ | $OCH_2Ph$ |
| 1,2-Ph | 1,2-Ph | 1,4-Ph | $CH_2CH_2$ | $CH_2OPh$ |
| 1,2-Ph | 1,2-Ph | 1,4-Ph | $CH_2CH_2$ | $CH_2Ph$ |
| 1,2-Ph | 1,2-Ph | 1,4-Ph | $CH_2CH_2$ | $C(CH_3)_2Ph$ |
| 1,2-Ph | 1,2-Ph | 1,4-Ph | $CH_2CH_2$ | $CH(CH_3)Ph$ |
| 1,2-Ph | 1,2-Ph | 1,4-Ph | $CH_2CH_2$ | $C(CH_3)_2CH_2Ph$ |
| 1,2-Ph | 1,2-Ph | 1,4-Ph | CH=CH | $C(CH_3)_2CH_2Ph$ |
| 4-F,1,2-Ph | 1,2-Ph | 1,4-Ph | $CH_2CH_2$ | $C(CH_3)_2CH_2Ph$ |
| 4,6-F,1,2-Ph | 1,2-Ph | 1,4-Ph | $CH_2CH_2$ | $C(CH_3)_2CH_2Ph$ |
| 1,2-Ph | 1,2-Ph | 1,4-Ph | $CH_2CH_2$ | (S)-$C(CF_3)(OCH_3)Ph$ |
| 1,2-Ph | 1,2-Ph | 1,4-Ph | $CH_2CH_2$ | (R)-$C(CF_3)(OCH_3)Ph$ |
| 1,2-Ph | 1,2-Ph | 1,4-Ph | $CH_2CH_2$ | $NCH_3(CH_2)_2Ph$ |
| 1,2-Ph | 1,2-Ph | 1,4-Ph | $CH_2CH_2$ | (S)-$NHCH(CH_3)Ph$ |
| 1,2-Ph | 1,2-Ph | 1,4-Ph | $CH_2CH_2$ | $NH(CH_2)_2$2-Thiophene |
| 1,2-Ph | 1,2-Ph | 1,4-Ph | $CH_2CH_2$ | (E)-CH=CHPh |
| 1,2-Ph | 1,2-Ph | 1,4-Ph | $CH_2CH_2$ | $NH(CH_2)_3CH_3$ |
| 5-Cl,1,2-Ph | 1,2-Ph | 1,4-Ph | $OCH_2$ | $NH(CH_2)_2$2-Thiophene |
| 1,2-Ph | 1,2-Ph | 1,4-Ph | $CH_2CH_2$ | $NHC(CH_3)_3$ |
| 1,2-Ph | 1,2-Ph | 1,4-Ph | $CH_2CH_2$ | $NHCH_2Ph$ |
| 1,2-Ph | 1,2-Ph | 1,4-Ph | $CH_2CH_2$ | o-Cl-Ph |
| 1,2-Ph | 1,2-Ph | 1,4-Ph | $OCH_2$ | $NH(CH_2)_2$2-Thiophene. |

* * * * *